US012653483B2

(12) United States Patent (10) Patent No.: US 12,653,483 B2
Gutjahr et al. (45) Date of Patent: Jun. 16, 2026

(54) METHOD FOR ACTUATING AN IMAGING DEVICE FOR ACQUIRING A CONTRAST AGENT-ENHANCED IMAGE DATA SET

(71) Applicant: Siemens Healthineers AG, Forchheim (DE)

(72) Inventors: Ralf Gutjahr, Nuremberg (DE); Bernhard Schmidt, Fuerth (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 364 days.

(21) Appl. No.: 17/479,253

(22) Filed: Sep. 20, 2021

(65) Prior Publication Data

US 2022/0096041 A1 Mar. 31, 2022

(30) Foreign Application Priority Data

Sep. 30, 2020 (DE) ..................... 10 2020 212 335.7

(51) Int. Cl.
*A61B 6/00* (2024.01)
*G06N 20/00* (2019.01)
*G16H 30/40* (2018.01)

(52) U.S. Cl.
CPC .............. *A61B 6/545* (2013.01); *A61B 6/481* (2013.01); *G06N 20/00* (2019.01); *G16H 30/40* (2018.01)

(58) Field of Classification Search
CPC ................................ A61B 6/545; A61B 6/481
See application file for complete search history.

(56) References Cited

U.S. PATENT DOCUMENTS

2008/0253634 A1* 10/2008 Hay ....................... A61B 6/504
600/431
2017/0181719 A1 6/2017 Korporaal et al.
(Continued)

FOREIGN PATENT DOCUMENTS

EP 3649955 A1 5/2020

OTHER PUBLICATIONS

Bae, K. T. et al. "Aortic and Hepatic Peak Enhancement at CT: Effect of Contrast Medium Injection Rate-Pharmacokinetic Analysis and Experimental Porcine Model", 1998, Radiology, vol. 206, pp. 455-464.

(Continued)

*Primary Examiner* — Boniface N Nganga
*Assistant Examiner* — Aminah Asghar
(74) *Attorney, Agent, or Firm* — Harness, Dickey & Pierce, P.L.C.

(57) ABSTRACT

A method includes provisioning an item of patient information of the patient via an interface; establishing, via a computing device, a first item of time information relating to a point in time of contrast enhancement by a contrast agent in at least one first subregion of the examination region based upon the item of patient information and by application of a trained function, at least one parameter of the trained function being adapted based upon a comparison between a first training item of time information based on a training item of patient information of a training patient and a first comparison item of time information, the first comparison item of time information being linked with the training item of patient information; and actuating, via a controller, the imaging device based upon the first item of time information established to acquire the contrast agent-enhanced image data set.

22 Claims, 4 Drawing Sheets

(56) References Cited

U.S. PATENT DOCUMENTS

| | | | |
|---|---|---|---|
| 2018/0071452 A1* | 3/2018 | Sharma | A61M 5/007 |
| 2019/0313990 A1 | 10/2019 | Sahbaee et al. | |
| 2020/0163639 A1 | 5/2020 | De Man et al. | |
| 2020/0334818 A1* | 10/2020 | Igarashi | G06V 10/80 |
| 2021/0015438 A1* | 1/2021 | Sahbaee Bagherzadeh | G16H 50/20 |
| 2021/0128818 A1* | 5/2021 | Vaz | A61B 6/507 |
| 2021/0133960 A1* | 5/2021 | Vaz | A61B 6/481 |
| 2021/0153827 A1* | 5/2021 | Lewis | G06F 3/04847 |
| 2021/0153830 A1* | 5/2021 | Vaz | A61B 6/54 |
| 2021/0386389 A1* | 12/2021 | Freiman | A61B 6/481 |
| 2022/0061793 A1* | 3/2022 | Vaz | A61B 6/54 |

OTHER PUBLICATIONS

K. Hornik: "Approximation Capabilities of Muitilayer Feedforward Networks", Technische Universifiit Wien, vol. 4, pp. 251-257, 1990.

Bae, K. T. et al. "Contrast Enhancement in Cardiovascular MDCT: Effect of Body Weight, Height, Body Surface Area, Body Mass Index, and Obesity", 2007, Vascular Imaging, DOI:10.2214/AJR. 07.2765.

Fleischmann Dominik et al.: "Mathematical Analysis of Arterial Enhancement and Optimization of Bolus Geometry for CT Angiography Using the Discrete Fourier Transform"; in: Journal of Computer Assisted Tomography, Lippincott Williams & Wilkins; 1999, vol. 23, No. 3, pp. 474-484; 1999.

Kyongtae T. Bae.: "Intravenous Contrast Medium Administration and Scan Timing at CT: Consideration and Approaches", in: Radiology, vol. 256, No. 1, Jul. 2010, pp. 32-61, DOI:10.1148/radiol. 10090908/-/DC1; 2010.

Sepp Hochreiter and Jurgen Schmidhuber, "Long short-term memory", in Neural computation 9.8, 1997, pp. 1735-1780.

Rumelhart, David E. et al.: "Learning representations by back-propagating errors"; in: Nature: vol. 323; pp. 533-536; 1986.

Mcculloch et al., "A Logical Calculus of the Ideas Immanent in Nervous Activity", Bulletin of Mathematical Biphysics, vol. 5, 1943, pp. 115-133; 1943.

Bae, K. T. "Peak Contrast Enhancement in CT and MR Angiography: When Does It Occur and Why? Pharmacokinetic Study in a Porcine Model", 2003, Radiology, vol. 227, pp. 809-816.

Hittmair et al. "Accuracy of Predicting and Controlling Time-Dependent Aortic Enhancement from a Test Bolus Injection", 2001, Journal of Computer Assisted Tomography, vol. 25, Nr. 2, pp. 287-294.

Rosenblatt, F. "The Perceptron: A Probabilistic Model For Information Storage And Organization In The Brain", 1958, Psychological Review, vol. 65, No. 6.

Korporaal, Johannes et al. "Evaluation of A New Bolus Tracking-Based Algorithm for Predicting A Patient-Specific Time of Arterial Peak Enhancement in Computed Tomography Angiography", 2015, Invest Radiol.

Hinzpeter, R. et al. "CT Angiography of the Aorta: Contrast Timing using a Fixed versus a Patient-Specific Trigger Delay", 2019, Radiology.

German Office Action for German Patent Application No. 102020212335.7 dated Jul. 2, 2021.

* cited by examiner

METHOD FOR ACTUATING AN IMAGING DEVICE FOR ACQUIRING A CONTRAST AGENT-ENHANCED IMAGE DATA SET

PRIORITY STATEMENT

The present application hereby claims priority under 35 U.S.C. § 119 to German patent application number DE102020212335.7 filed Sep. 30, 2020, the entire contents of which are hereby incorporated herein by reference.

FIELD

Example embodiments of the invention generally relate to a method for actuating an imaging device for acquiring a contrast agent-enhanced image data set, to an associated apparatus for actuating an imaging device, to an associated imaging device and to an associated computer program product. Example embodiments of the invention furthermore relate to a training method for providing a trained function for application in a method for actuating a medical imaging device, to an associated training apparatus, and to an associated computer program product.

BACKGROUND

Modern imaging methods are frequently used to generate two- or three-dimensional image data which can be used for visualizing a mapped object under examination and furthermore also for further applications. The imaging methods are frequently based on the acquisition of X-rays, wherein "measured projection data" is generated. Measured projection data may, for example, be acquired with the assistance of a computed tomography device (CT device). In CT systems, a gantry-mounted combination of an X-ray source and, arranged opposite, an X-ray detector usually travels around a measurement space in which the object under examination (hereinafter denoted patient without limitation of general applicability) is located. The center of rotation (also known a "isocenter") here coincides with a "system axis", also known as z axis, which extends in the z direction. Over the course of one or more revolutions, the patient is transilluminated with X-rays from the X-ray source, wherein measured projection data or X-ray projection data is acquired with the assistance of the opposing X-ray detector.

Current clinical practice is frequently to perform imaging examinations using contrast agents, for example an intravenously administered contrast agent based on iodine, in order to improve the visibility of blood vessels, organ tissue, tumorous structures or bleeding. These are likewise used for monitoring of treatment. Suitable selection of the contrast agent injection protocol and also of the scan protocol are here essential in order to generate high-quality image data sets which are optimal for diagnosis and simultaneously to avoid unnecessarily burdening the patient with regard to an administered radiation dose and likewise also with regard to a contrast agent dose.

One important parameter here is the optimum time window or optimum starting time for acquisition of the measurement data in particular as a function of injection timing, also known as scan timing, which has to be coordinated with the time-dependent distribution of the contrast agent in the body of the particular patient. A distinction is here drawn between different perfusion phases of contrast agent enhancement. Imaging at different points in time, i.e. during different perfusion phases, may in particular facilitate different diagnoses. A distinction is generally drawn at least between what is known as an "arterial phase", which can be subdivided into an early and a late arterial phase, a hepatic portal venous phase, a nephrogenic phase and a delayed phase/equilibrium phase.

In clinical practice, scan timing determination can be improved by using a "test bolus" or "bolus tracking" method. In the case of a test bolus method, prior to use in the course of imaging, a small quantity of contrast agent, the test bolus, is used to map a region to be examined via a series of image data sets which map the region to be examined at least in time-resolved manner and to observe the arterial inflow of the contrast agent based upon the time profile of intensity values acquired in a local artery. On this basis, it is possible to determine the time of local arrival of the test bolus and also the time of maximum concentration in the local arteries. However, larger volumes of contrast agent are required for the subsequent imaging, as a result of which the course of contrast agent enhancement, in particular the time of maximum contrast enhancement, is affected. Furthermore, the test bolus volume used is itself too low in order to observe enhancement in an extravascular region, for example in liver tissue, which may be of relevance to diagnosis. For the purposes of scan timing, empirical experience is therefore generally used in order suitably to adapt the time values for local arterial enhancement established via a test bolus method based upon fixed time delays and depending on a clinical situation.

A bolus tracking method merely involves injecting a contrast agent bolus. The optimum scan timing is determined by monitoring the arterial inflow of contrast agent in the region to be examined by way of time-resolved image data sets and with the assistance of the acquired intensity values. If a user-defined threshold value is exceeded at the location of inflow monitoring, the diagnostic scan is initiated with a fixed time delay which is intended to take account of the time offset between the threshold value being exceeded and optimum contrast enhancement. As for the test bolus method, the fixed delay is generally likewise set based upon empirical experience depending on the clinical situation.

Both of the previously described methods make use of empirical knowledge in order to estimate an improved scan timing. This is generally performed based upon empirical values averaged over a large patient population. No or only very little account is generally taken of patient-specific adaptation. Furthermore, the portion of the population on which this adaptation is based is a matter for the user. Whether based on internally established knowledge or for example literature knowledge, this is frequently left up to the individual user, which can result in major variability and results which are difficult to compare.

Pharmacokinetic models may furthermore be used in order to enable more individualized scan timing. Physiologically based pharmacokinetic modeling is a mathematical modeling technique for predicting the absorption, distribution, metabolism and excretion of synthetic or natural chemical substances in humans and other animal species. Such a model may accordingly also be used in order to establish indications for local contrast agent distributions in the patient over time. The proposed methods are, however, in particular limited to an arterial perfusion phase. It should furthermore be noted that, in particular when taking account of more detailed items of patient information, such modeling can be computationally intensive and time-consuming and, in particular if this is to be used in conjunction with a bolus tracking method, it has to be used simultaneously with the actual scan. This results in time limitations for modeling and in particular also limitations for taking account of the influence of patient-specific parameters.

Examples and applications of such modeling may be found, for example, in Fleischmann et al. (Fleischmann D, Hittmair K. Mathematical analysis of arterial enhancement and optimization of bolus geometry for CT angiography using the discrete Fourier transform, Journal of Computer Assisted Tomography 1999; 23(3):474-84.), Hittmair et al. (Hittmair K, Fleischmann D. Accuracy of predicting and controlling time-dependent aortic enhancement from a test bolus injection. Journal of Computer Assisted Tomography 2001; 25(2):287-94), Korporaal et al. (Korporaal J G, Bischoff B, Arnoldi E, et al. Evaluation of A New Bolus Tracking-Based Algorithm for Predicting A Patient-Specific Time of Arterial Peak Enhancement in Computed Tomography Angiography. Investigative Radiology 2015; 50(8): 531-8), Hinzpeter et al. (Hinzpeter R, Eberhard M, Gutjahr R, et al. C T Angiography of the Aorta: Contrast Timing by Using a Fixed versus a Patient-specific Trigger Delay. Radiology 2019; 291(2):531-8).

SUMMARY

Embodiments of the present invention provide an improved method and an improved apparatus for actuating an imaging device in a patient-specific manner for the generation of a contrast agent-enhanced image data set.

Further advantageous and in part per se inventive embodiments and further developments of the invention are described in the claims and the following description.

At least one embodiment of the invention relates to a method for actuating an imaging device for the acquisition of a contrast agent-enhanced image data set of an examination region of a patient at least comprising provision, establishment and actuation.

In the provision, an item of patient information of the patient is provided via an interface.

In the establishment, a first item of time information relating to a point in time of contrast enhancement by a contrast agent in at least one first subregion of the examination region is established via a computing unit. Establishment is based on the patient information and comprises the application of a trained function, wherein at least one parameter of the trained function is adapted based upon a comparison between a first training item of time information based on a training item of patient information of a training patient and a first comparison item of time information, wherein the first comparison item of time information is linked with the training item of patient information.

In the actuation, the imaging device is actuated based upon the established first item of time information via a control unit, wherein the contrast agent-enhanced image data set is acquired.

The invention of at least one embodiment furthermore relates to a training method for a trained function for use in a method for actuating an imaging device as claimed in one of the preceding claims comprising the steps of:

first provision of a training item of patient information and a first comparison item of time information linked therewith via a first training interface, application of the trained function to the provided training item of patient information and thus establishment of a first training item of time information via a training computing unit, adaptation of at least one parameter of the trained function based upon a comparison of the training item of time information and the corresponding first comparison item of time information via the training computing unit, second provision of the trained function via a second training interface.

At least one embodiment of the invention further relates to an apparatus for actuating an imaging device for the acquisition of a contrast agent-enhanced image data set of an examination region of a patient according to a previously described method and the aspects thereof, comprising:

an interface configured to provide an item of patient information of the patient, a computing unit configured to establish a first item of time information relating to a point in time of contrast enhancement by the contrast agent in at least one first subregion of the examination region, based upon the item of patient information by application of a trained function, wherein at least one parameter of the trained function is adapted based upon a comparison between a first training item of time information based on a training item of patient information of a training patient and a first comparison item of time information, wherein the first comparison item of time information is linked with the training item of patient information, and a control unit configured to actuate the imaging device based upon the first item of time information.

At least one embodiment of the invention furthermore relates to an imaging device comprising an apparatus for actuating an imaging device.

The imaging device is here advantageously configured to carry out an embodiment of the proposed method for actuating the imaging device. The advantages of the proposed imaging device substantially correspond to the advantages of the proposed method for actuating the imaging device. Features, advantages or alternative embodiments mentioned in this connection are likewise also applicable to the imaging device and vice versa.

The imaging device may preferably be configured as a CT device.

At least one embodiment of the invention further relates to a training apparatus for providing a trained function for application in a previously described method for actuating a imaging device comprising:

a training interface, configured to provide a training item of patient information and a first comparison item of time information linked therewith, a training computing unit configured to apply the trained function to the provided training item of patient information and thus establish a first training item of time information, wherein the training computing unit is furthermore configured to adapt at least one parameter of the trained function based upon a comparison of the first training item of time information and the corresponding first comparison item of time information, and a second training interface configured to provide the trained function.

Such a training apparatus may in particular be configured to carry out the previously described training method according to the invention for providing a trained function and the aspects thereof. The training apparatus is configured to carry out this method and the aspects thereof by the training interface and the training computing unit being configured to carry out the corresponding method steps.

Features, advantages or alternative embodiments mentioned in this connection are likewise also applicable to the training apparatus and vice versa.

At least one embodiment of the invention furthermore relates to a computer program product with a computer program, which can be directly loaded into a storage device of an apparatus for actuating an imaging device, with program parts for carrying out all the steps of one embodiment of the method for actuating an imaging device and the aspects thereof when the program parts are run by the apparatus.

At least one embodiment of the invention furthermore relates to a computer program product with a computer program, which can be directly loaded into a training storage device of a training apparatus, with program parts for carrying out all the steps of at least one embodiment of the training method and the aspects thereof when the program parts are run by the training apparatus.

A computer program product may be a computer program or comprise a computer program. As a consequence, the method according to at least one embodiment of the invention can be carried out in a quick, identically repeatable and robust manner. The computer program product is configured such that it can carry out the method steps according to the invention via the apparatus or training apparatus. The apparatus or training apparatus must here in each case have the prerequisites such as for example an appropriate working memory, an appropriate graphics card or an appropriate logic unit for it to be possible to carry out the respective method steps efficiently. The computer program product is for example stored on a computer-readable medium or stored on a network or server from which it can be loaded into a computing unit or training computing unit of the apparatus or training apparatus.

At least one embodiment of the invention may relate to a computer-readable storage medium on which program parts that can be read and run by the apparatus are stored in order to carry out all the steps of one of at least one embodiment of the methods for actuating an imaging device or the aspects thereof when the program parts are run by the apparatus.

Examples of a computer-readable data storage medium are a DVD, a magnetic tape, a hard disk or a USB stick on which electronically readable control information, in particular software, is stored.

At least one embodiment of the invention may relate to a computer-readable storage medium on which program parts that can be read and run by a training apparatus are stored in order to carry out all the steps of at least one embodiment of the described training method or one of the aspects thereof when the program parts are run by the training apparatus.

At least one embodiment of the invention is directed to a method for actuating an imaging device for acquisition of a contrast agent-enhanced image data set of an examination region of a patient, the method comprising:

provisioning an item of patient information of the patient via an interface;

establishing, via a computing device, a first item of time information relating to a point in time of contrast enhancement by a contrast agent in at least one first subregion of the examination region based upon the item of patient information and by application of a trained function, at least one parameter of the trained function being adapted based upon a comparison between a first training item of time information based on a training item of patient information of a training patient and a first comparison item of time information, the first comparison item of time information being linked with the training item of patient information; and actuating, via a controller, the imaging device based upon the first item of time information established, wherein the contrast agent-enhanced image data set is acquired.

At least one embodiment of the invention is directed to a training method for the provision a trained function for a method for actuating an imaging device, comprising:

provisioning, via a first training interface, a training item of patient information and a first comparison item of time information linked to the training item of patient information;

applying, via a training computing device, the trained function to a training item of patient information to establish a first training item of time information;

adapting, via the training computing device, at least one parameter of the trained function based upon a comparison of the first training item of time information and a corresponding first comparison item of time information; and provisioning, via the first training interface or a second training interface, the trained function.

At least one embodiment of the invention is directed to an apparatus for actuating an imaging device for acquisition of a contrast agent-enhanced image data set of an examination region of a patient, comprising:

an interface configured to provide an item of patient information of the patient;

a computing unit configured to establish a first item of time information relating to a point in time of contrast enhancement by the contrast agent in at least one first subregion of the examination region, based upon the item of patient information by application of a trained function, at least one parameter of the trained function being adapted based upon a comparison between a first training item of time information based on a training item of patient information of a training patient and a first comparison item of time information, the first comparison item of time information being linked with the training item of patient information; and a controller, configured to actuate the imaging device based upon the first item of time information.

At least one embodiment of the invention is directed to a training apparatus for providing a trained function for application for actuating an imaging device, comprising:

a first training interface, configured to provide a training item of patient information and a first comparison item of time information linked with the training item of patient information;

a training computing unit configured to apply the trained function to the provided training item of patient information to establish a first training item of time information, and adapt at least one parameter of the trained function based upon a comparison of the first training item of time information and the corresponding first comparison item of time information; and a second training interface configured to provide the trained function.

At least one embodiment of the invention is directed to a non-transitory computer program product storing a computer program, directly loadable into a storage device of an apparatus for actuating an imaging device, including program parts for carrying out the method of an embodiment when the program parts are run by the apparatus.

At least one embodiment of the invention is directed to a non-transitory computer program product storing a computer program, directly loadable into a training storage device of a training apparatus, including program parts for carrying out the method of an embodiment when the program parts are run by the training apparatus.

BRIEF DESCRIPTION OF THE DRAWINGS

The invention is explained below with reference to example embodiments and to the appended figures. The depiction in the figures is schematic, highly simplified and not necessarily true to scale. In the figures.

DETAILED DESCRIPTION OF THE EXAMPLE EMBODIMENTS

Figures 1, 2:
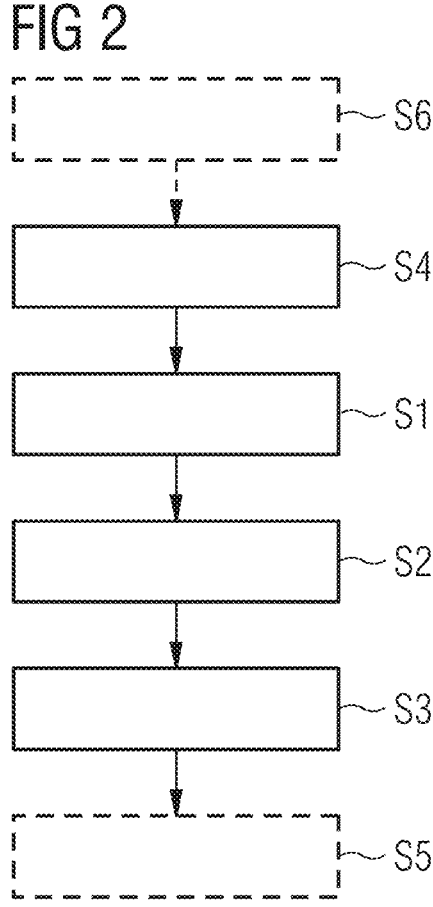
FIG. 1 shows a schematic flow chart for an example method variant of an embodiment for actuating an imaging device.
FIG. 2 shows a schematic flow chart for a further example method variant of an embodiment for actuating an imaging device.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for actuating an imaging device for the acquisition of a contrast agent-enhanced image data set of an examination region of a patient at least comprising provision, establishment and actuation.

In the provision, an item of patient information of the patient is provided via an interface.

In the establishment, a first item of time information relating to a point in time of contrast enhancement by a contrast agent in at least one first subregion of the examination region is established via a computing unit. Establishment is based on the patient information and comprises the application of a trained function, wherein at least one parameter of the trained function is adapted based upon a comparison between a first training item of time information based on a training item of patient information of a training patient and a first comparison item of time information, wherein the first comparison item of time information is linked with the training item of patient information.

In the actuation, the imaging device is actuated based upon the established first item of time information via a control unit, wherein the contrast agent-enhanced image data set is acquired.

The imaging device may be configured as a CT device, wherein, with relative rotational movement between the X-ray source and the patient, a large number of items of measured projection data are acquired. Based upon the measured projection data, it is possible to reconstruct a three-dimensional image data set or one or a plurality of two-dimensional tomographic image data sets of the examination region (for example via a filtered backprojection reconstruction algorithm or via an iterative reconstruction algorithm). In the case of an extensive examination region, the patient is displaced relative to the X-ray detector/X-ray source combination such that measured projection data can be acquired from the entire examination region. A helical scan with the patient being continuously advanced during acquisition of the measured projection data is frequently used here. There are, however, also sequential capture modes in which the patient is displaced sequentially relative to the X-ray detector/X-ray source combination. Alternatively, the imaging device may also for example be a C-arm X-ray machine, an angiography device or a mammography device. However, other imaging devices which are configured to generate a two-dimensional or also three-dimensional image data set of the patient, for example via a magnetic tomography device or an ultrasound device, are also conceivable.

The image data set generated by way of the method may in particular be a three-dimensional image data set (3D image data set) or a two-dimensional image data set (2D image data set). A 2D image data set permits a two-dimensional, in particular spatially two-dimensional, depiction of an examination region of the patient. A 3D image data set permits a three-dimensional, in particular spatially three-dimensional, depiction of an examination region of the patient. A three-dimensional image data set may also be presented as a number of tomographic image data sets. A tomographic image data set in each case comprises a slice of the 3D image data set at a position along a highlighted axis. A tomographic image data set then in each case permits a two-dimensional, in particular spatially two-dimensional, presentation of the respective slice of the 3D-image data set. A 3D image data set advantageously comprises a plurality of voxels, in particular image points. Each voxel may here preferably in each case have a value, in particular an image value, for example a grayscale value and/or an RGB color value and/or an intensity value. Similarly, a two-dimensional image data set may comprises a plurality of pixels, in particular image points. Each pixel may here preferably in each case have a value, in particular an image value, for example a grayscale value and/or an RGB color value and/or an intensity value.

A contrast agent-enhanced image data set may in particular designate an image data set which is based on the acquisition of the measurement data underlying the image data set, wherein a contrast agent is used during the acquisition thereof in order to obtain improved contrast of relevant structures relative to a surrounding tissue in the generated image data set for improved diagnosis. In other words, a contrast agent-enhanced image data set makes use of contrast enhancement achieved by a previously administered contrast agent. A contrast agent-enhanced image data set is in particular based on a contrast agent having been administered, for example injected intravenously, to a patient prior to acquisition of the measurement data underlying the image data set. A contrast agent can advantageously improve the visibility of blood vessels, organ tissue or tumorous structures in the generated image data set.

Contrast agent-enhanced image data sets which maps the examination region at different points in time after contrast agent administration, i.e. during different perfusion phases after a contrast agent injection, may in particular enable different diagnoses. The arterial phase relates to diffusion from the large arteries into the small arteries, arterioles and capillaries.

Vascular damage (for example aortic dissection or arterial bleeding) may advantageously be diagnosed with the assistance of image data sets from the "early" arterial phase. Hypervascular lesions, focal nodular hyperplasia or a hepatocellular carcinoma or an adenoma may, for example, be more readily visible in a "late" arterial phase, Hypovascular liver lesions, such as cysts, abscesses or metastases may, for example, be more readily visible in a hepatic portal venous phase which is particularly important in liver imaging. Diagnosis of renal cell carcinoma may, for example, be facilitated during a nephrogenic phase, which is particularly important for kidney imaging, due to enhancement of the renal parenchyma. Fibrotic lesions, cholangiocarcinoma, fibrotic metastases or transitional cell carcinoma may, for example, be more readily visible in a delayed/equilibrium phase. Scan timing coordinated with the perfusion phase is extremely advantageous for differential diagnosis. The formation of a particular perfusion phase may here be patient-specific, since account has to be taken of various patient-specific factors which influence the patient's hemodynamics and the intravenous, intracellular and extracellular contrast distribution. Patient-specific scatter here becomes more pronounced with an increasing time profile i.e. in particular for later perfusion phases. It should furthermore be borne in mind that patient-specific scatter also increases with increasing distance from an injection site or from a region which is used for establishing time values by way of a test bolus method or bolus tracking method. The latter may for be of relevance if the examination region is extensive and an item of time information is established in one subregion of the examination region by way of one of the above-stated methods but the scan timing is also to be coordinated for an examination region subregion differing and in particular remote therefrom.

The patient may be a human patient and/or an animal patient. The examination region may in particular be the region which is mapped by way of the image data set. An examination region of a patient comprised, i.e. represented, by the image data set may comprise an anatomical and/or spatial region of the patient which comprises a predetermined tissue region and/or a spatial region necessary for diagnosis. The examination region may here comprise a body region, for example the head or thorax, of the patient. The examination region may optionally also comprise the patient's entire body.

The provided patient information comprises at least one patient-specific parameter, preferably a plurality of patient-specific parameters. The patient information preferably comprises possible influencing factors on (in particular time-dependent) contrast agent distribution in the examination region of the patient. An item of patient information may for example relate to a physiological feature of the patient in question, an item of information with regard to a disease or symptoms which have occurred or with regard to a surgical intervention. The patient information may comprise laboratory values or medication for the patient. The patient information may in particular also comprise parameters which relate to the injection of the contrast agent or the contrast agent itself. The provided patient information may in particular comprise an item of information about one (or a plurality of) target organ(s) of relevance to the diagnosis, for example the liver, kidney, lung or brain. The patient information preferably comprises a plurality of patient-specific parameters. Patient information which is as comprehensive as possible and specifies the patient and the conditions for the generation of the contrast agent-enhanced image data set may in particular result in improved patient-specific establishment of the first item of time information. The patient information preferably comprises at least one item of information about the subregion which relates to the first item of time information to be established.

Provision of the patient information may for example involve acquisition and/or reading out of a computer-readable data storage device and/or receipt from a storage unit via the first interface. The patient information may be based on a patient record. The patient information may be acquired or at least supplemented by clinical personnel questioning the patient prior to generation of the image data set and be provided for actuation. The patient information may be provided based upon parameters which are input by clinical personnel or are fixedly predetermined for the examination protocol for generation of the image data set.

According to at least one embodiment of the invention, the first item of time information relates to a point in time of contrast enhancement in at least one first subregion of the examination region. The at least one subregion may comprise an anatomical and/or spatial region of the patient which comprises a predetermined tissue region and/or spatial region necessary for diagnosis. The first subregion may in particular comprise a region of the examination region which is of particular relevance to diagnosis. The at least one subregion may in particular comprise a specific (target) organ or a plurality of (target) organs of a patient. A target organ may be of particular relevance to diagnosis by way of the image data set to be generated. The at least one subregion in particular comprises the region of the patient which is of relevance to diagnosis and is to be presented, preferably optimally, by way of the image data set. The at least one subregion may be identical to the examination region.

The point in time of contrast enhancement may here in particular comprise or relate to a point in time of a perfusion phase at least in the subregion after contrast agent administration. The point in time may relate to a beginning of a perfusion phase or an end of a perfusion phase or a time window of a perfusion phase. The point in time may relate to an optimum contrast enhancement in the subregion during a perfusion phase if an image data set is to be generated at this point in time. Optimum may in particular mean optimum for diagnosis, i.e. that the structures of relevance to diagnosis in the subregion are optimally visible in the generated image data set, i.e. the best possible contrast relative to surrounding tissue is obtained. The relevant structures may here in particular be pathological changes, for example tumorous tissue, within healthy tissue. The point in time may comprise a maximum contrast enhancement of relevant structures in the subregion. A first item of time information may for example relate to a point in time of a hepatic portal venous phase, a nephrogenic phase or a delayed phase.

The first item of time information relating to a point in time of contrast enhancement may involve the time information itself corresponding to this point in time. It may, however, also involve the first item of time information being usable in order to determine an improved patient-specific point in time of contrast enhancement. The first item of time information may approximately correspond to an adaptation factor. For example, a second item of time information may be present in the form of a point in time and the first item of time information in the form of an adaptation factor, which may be used for adapting the second item of time information in such a manner that a point in time of contrast enhancement is established in a more patient-specific manner. The time information or the point in time to which the time information relates may in particular comprise a relative time indication, for example a point in time relative to a point in time of a contrast agent injection or relative to a point in time of a threshold value being exceeded if a combination with a bolus tracking method is used.

An item of information at least over the first subregion is preferably included in the establishment of the first item of time information. This may comprise an item of information about a target organ. This may be a location in the first subregion relative to the examination region and/or to an injection site of a contrast agent injection and/or a second subregion of the examination region.

A trained function may preferably be implemented via an artificial intelligence system, i.e. by a machine learning method. Establishment based upon the application of a trained function allows better account to be taken of all the relevant influencing variables for establishment, including those for which a user, in particular for example also a less highly trained or less experienced user, cannot estimate any correlation with establishment or can do so only with difficulty. In particular, it is here possible to take account of a large number of parameters and influencing variables which mathematical modeling via a pharmacokinetic model can take into account only with very considerable effort, if at all, if correlations cannot straightforwardly be understood and thus mapped in a mathematical model. An artificial intelligence system may be taken to be a system for artificially generating knowledge from experience. An artificial system learns from examples in a training phase and, once the training phase is complete, is capable of generalizing. Using such a system may involve the recognition of patterns and regularities in the training data. After the training phase, the artificial intelligence system can extract, for example from previously unknown measurement data, features or parameters which enter into the derivation. After the training phase, the optimized, i.e. trained, algorithm can estimate suitable measurement parameters for actuation, for example based upon a previously unknown item of patient information. The artificial intelligence system may be based on an artificial neural net or also on another machine learning method. In particular, after the training phase, a trained function based on an artificial intelligence system can automatically establish the first item of time information in a particularly reliable and time-efficient manner.

A trained function in particular maps input data onto output data. The output data may here in particular furthermore be dependent on one or more parameters of the trained function. The one or more parameters of the trained function may be determined and/or adapted by training. Determination and/or adaptation of the one or more parameters of the trained function may in particular be based on a pair composed of training input data and associated, i.e. linked, comparison output data, wherein the trained function is applied to the training input data to generate training output data. In particular, determination and/or adaptation may be based on a comparison of the training output data and the training comparison data. In general, a trainable function, i.e. a function with one or more parameters which are not as yet adapted, is also denoted a trained function.

Other terms for trained function are trained mapping rule, mapping rule with trained parameters, function with trained parameters, algorithm based on artificial intelligence or machine learning algorithm. One example of a trained function is an artificial neural network, wherein the edge weights of the artificial neural network correspond to the parameters of the trained function. The term "neural net" may also be used instead of the term "neural network". In particular, a trained function may also be a deep artificial neural network or deep neural network. Examples of a neural net may be a "feedforward neural network" (Hornik K. Approximation capabilities of multilayer feedforward networks. Neural networks 1991; 4(2):251-7, Rosenblatt F. The perceptron: a probabilistic model for information storage and organization in the brain. Psychological review 1958; 65(6):386, McCulloch W S, Pitts W. A logical calculus of the ideas immanent in nervous activity. The Bulletin of Mathematical Biophysics 1943; 5(4):115-33) or a recurrent neural net (Rumelhart D E, Hinton G E, Williams R J. Learning representations by back-propagating errors. Nature 1986; 323(6088):533-6, Hochreiter S, Schmidhuber J. Long short-term memory. Neural Computation 1997; 9(8):1735-80.). In particular, combinations of different types can be used; and the entire contents of each of the aforementioned documents are hereby incorporated herein by reference.

The trained function may in particular be trained via backpropagation. First of all, training output data can be determined by applying the trained function to the training input data. A deviation between the training output data and the training comparison data may then be established by applying an error function to the training output data and the training comparison data. Furthermore, at least one parameter, in particular a weighting, of the trained function, in particular of the neural network, may be iteratively adapted based upon a gradient of the error function with regard to the at least one parameter of the trained function. As a result, the deviation between the training output data and the training comparison data can advantageously be minimized during the training of the trained function.

The trained function, in particular the neural network, advantageously has an input layer and an output layer. The input layer may here be configured to receive input data. The output layer may furthermore be configured to provide output data. The input layer and/or the output layer may here in each case comprise a large number of channels, in particular neurons.

According to at least one embodiment of the invention, the input data for the trained function may comprise the provided patient information of the patient. The patient information may preferably comprise a plurality of patient-specific patient parameters. According to the invention, the output data may in particular comprise the first item of time information.

According to at least one embodiment of the invention, in the training phase of the trained function, a training item of patient information, preferably a plurality of training items of patient information, of a training patient, preferably of a plurality of training patients, is/are in particular used as training input data. On this basis, a first training item of time information may be established as training output data. Furthermore, at least one parameter of the trained function can be adapted to a comparison of the established training item of time information of the training patient with a first comparison item of time information as training comparison data.

The training input data and the training comparison data are linked together.

The training input data and training comparison data may in particular be based on a real patient population. In other words, a training item of patient information may be based on a real item of patient information of a real patient. The training item of patient information of a respective training patient preferably comprises a maximally comprehensive patient-specific parameter set. The training item of patient information which is available for a respective training patient may here comprise different patient-specific parameters. The training comparison data may for example be established from, preferably time-resolved, image data sets of the training patient using contrast agent, from which a point in time of a contrast agent enhancement can be extracted at least in a subregion, preferably at different points in time, i.e. for different perfusion phases.

The at least first item of time information may be established, in particular automatically, via a computing unit, i.e.

there may be no need for user interaction. For this purpose, the computing unit advantageously has a storage device onto which program code means can be loaded. The program code means in particular include program code which enables establishment of the at least one first item of time information when an item of patient information of the patient is provided.

Establishment by way of the trained function is particularly advantageous because the first item of time information for the provided item of patient information and thus for each patient can be individually and automatically established. After the training phase, application of a trained function here enables particularly time-efficient establishment, in particular also when a plurality of patient parameters are taken into account.

Advantageously, the established first item of time information may accordingly permit patient-specific actuation of the imaging device, such that the measurement data on which the contrast-enhanced image data set is based can be acquired at a point in time which is in particular suitable for an optimum diagnosis. It is thus possible to enable scan timing which is optimal for a patient because the first item of time information is not selected from predetermined parameters averaged over a patient group or with the assistance of simplified correlations which may be correct at most on average.

According to a preferred variant of at least one embodiment of the method, the first subregion comprises an extravascular part of the examination region and the first item of time information relates to a point in time of contrast enhancement during a perfusion phase subsequent to an arterial perfusion phase of contrast enhancement by the contrast agent.

As already previously described, an image data set which maps the examination region during a specific perfusion phase in the at least one subregion may in particular permit a more differentiated diagnosis. The optimum point in time of contrast enhancement relating to a particular perfusion phase is patient-specific, since various patient-specific factors which influence the patient's hemodynamics and the intravenous, intracellular and extracellular contrast distribution have to be taken into account. Patient-specific scatter here becomes more pronounced with an increasing time profile i.e. in particular for later perfusion phases and correspondingly for an extravascular region. An extravascular region may in particular comprise a tissue region of a target organ, for example the liver, kidney, lung, brain etc. Existing methods generally rely on empirical values averaged over a broad patient population for temporal adaptation of an examination protocol, which do not permit patient-specific establishment or only with major input of time or computing effort, in particular if a large number of parameters are to be taken into account.

Advantageously, by applying a trained function, the method according to at least one embodiment of the invention permits time-efficient and robust establishment of a patient-specific and thus optimized first item of time information, in particular also for a perfusion phase subsequent to an arterial perfusion phase. This advantageously permits optimum coordination of imaging device actuation for optimum contrast enhancement in an extravascular subregion.

According to a further method variant of at least one embodiment, the method moreover comprises the provision of a second item of time information via a second interface, wherein the second item of time information relates to a point in time of contrast enhancement during an arterial perfusion phase of contrast enhancement at least in the first or in a second subregion, differing from the first, of the examination region, and wherein actuation is based on the first item of time information and the second item of time information.

The second item of time information may for example be based on a bolus tracking method or a test bolus method and/or be based on a pharmacokinetic model. For example, a second subregion may comprise a region of a determination of the second item of time information in the examination region by way of a bolus tracking method or test bolus method.

A conventional method, for example based upon a bolus tracking method, a test bolus method and/or a pharmacokinetic model, is capable of ensuring, at least for the second item of time information, a sufficiently good determination of the second item of time information relating to arterial enhancement. As already described, the point in time of contrast enhancement relating to a respective perfusion phase may be patient-specific since various patient-specific factors have an influence. Patient-specific scatter here becomes more pronounced with an increasing time profile i.e. in particular for later perfusion phases and for the profile of contrast enhancement in extravascular regions. Equally, patient-specific scatter is intensified if a relevant first subregion is located remotely from a second subregion for or in which the second item of time information has been determined.

The first item of time information, which relates to a point in time of contrast enhancement during a perfusion phase subsequent to an arterial perfusion phase of contrast enhancement by the contrast agent, may serve to adapt the second item of time information in order, based upon the second item of time information, to establish a point in time of contrast enhancement during a perfusion phase subsequent to an arterial perfusion phase. In other words, the established first item of time information may comprise a time adaptation factor, by which the first item of time information can be adapted in order to obtain an adapted item of time information. The imaging device may then be actuated based upon the adapted item of time information. For example, adaptation may involve simply summing the first and the second items of time information. There may, however, also be other variant embodiments. A time adaptation factor may also enter into a multiplication or another adaptation.

The second item of time information may also enter into the establishment of the first item of time information, such that the first item of time information already represents an adapted item of time information, based upon which the imaging device can be actuated. For example, the first item of time information can be established based upon the item of patient information and the second item of time information. For example, the second item of time information may be an input parameter of the trained function.

The first item of time information and the second item of time information may preferably be determined temporally in parallel, such that a particularly time-efficient procedure can be ensured.

This method variant of at least one embodiment can advantageously exploit the fact that a second "rough" item of time information, on which the method according to the invention can be based, is already available and merely patient-specific adaptation need be carried out. It is advantageously possible to start from patient-specific measured values for an arterial phase, for example via a bolus tracking method or a test bolus method and/or a pharmacokinetic model and, following thereon, to establish a patient-specific point in time of a contrast enhancement of a perfusion phase subsequent to an arterial perfusion phase in a time-efficient and robust manner. This may advantageously constitute a particularly robust determination of an item of time information for actuating the imaging device.

According to a further method variant of at least one embodiment, the method moreover comprises the step of providing a second item of time information via a second interface, wherein the second item of time information relates to a point in time of contrast enhancement during an arterial perfusion phase of contrast enhancement at least in a second subregion, differing from the first, of the examination region, and wherein the first item of time information relates to a point in time of contrast enhancement during an arterial perfusion phase of contrast enhancement at least in the first subregion, and actuation is based on the first item of time information and the second item of time information.

The second item of time information may for example be based on a bolus tracking method or a test bolus method and/or be based on a pharmacokinetic model. For example, the second subregion comprises a location of a determination of the second item of time information in the examination region based upon a bolus tracking method or test bolus method. The method according to the invention also advantageously makes it possible to take better account of patient-specific scatter of a point in time of an arterial perfusion phase if a first relevant subregion is remote from a second subregion, for or in which the second item of time information has been determined.

In the same manner as previously described in the variant embodiment, the first item of time information may serve to adapt the second item of time information in order, based upon the second item of time information, to determine a point in time of contrast enhancement during an arterial perfusion phase in a subregion remote from the first subregion. The established first item of time information may comprise a time adaptation factor, by which the first item of time information can be adapted in order to obtain an adapted item of time information. The second item of time information may enter into the establishment of the first item of time information. It is advantageously possible to exploit the fact that a second "rough" item of time information, on which the method can be based, is already available and merely patient-specific adaptation need be carried out.

If a second item of time information also enters into the establishment of the first item of time information, the establishment of the first item of time information by application of the trained function according to a method variant may moreover be based on the second item of time information, and at least one parameter of the trained function is adapted based upon a comparison between, on the one hand, a first training item of time information based on a training item of patient information and a second training item of time information of a training patient and, on the other, a first comparison item of time information, wherein the first comparison item of time information is linked with the training item of patient information and the second training item of time information.

Account may advantageously be taken of the second item of time information during establishment. An adapted item of time information may advantageously also be provided by the establishment.

According to one method variant of at least one embodiment, the second item of time information is based on a pharmacokinetic model in conjunction with a test bolus method or in conjunction with a bolus tracking method.

By way of a pharmacokinetic model in conjunction with a test bolus or bolus tracking method, it is possible to provide a particularly advantageous second item of time information which can ensure a particularly reliable second item of time information.

According to one method variant of at least one embodiment, the patient information comprises at least one parameter from the following list:

a parameter of patient physiology, a parameter of patient pathology, a laboratory value for the patient, patient medication, a parameter of the contrast agent used or of contrast agent administration, a (target) organ to be mapped by way of the contrast-enhanced image data set.

A parameter of patient physiology may for example comprise inter alia the patient's age, gender, height, weight, cardiac output or blood volume. A parameter of patient pathology may for example comprise hyper- or hypotonia, vascular resistance, peripheral vascular resistance, an item of information about a previous surgical intervention or also an item of information about a family history with regard to existing disease. A laboratory value may comprise a hematocrit value or a laboratory value established via an ELISA test system ("enzyme-linked immunosorbent assay") or another laboratory value. Patient medication may for example comprise whether β blockers or the like are being taken. A parameter of the contrast agent used or of contrast agent administration may comprise a contrast agent concentration, an osmolality or rheology of the contrast agent, the site of contrast agent injection, a contrast agent volume, a duration of contrast agent administration or a rate of injection of the contrast agent.

Examples of a correlation between various patient-specific parameters have been investigated for example in Bae K T: Intravenous contrast medium administration and scan timing at CT: considerations and approaches 1 (Radiology 2010; 256(1):32-61), Bae K T: Peak contrast enhancement in CT and MR angiography: when does it occur and why? Pharmacokinetic study in a porcine model (Radiology 2003; 227(3):809-16), Bae K T, Heiken J, Brink J: Aortic and hepatic peak enhancement at CT: effect of contrast medium injection rate-pharmacokinetic analysis and experimental porcine model (Radiology 1998; 206(2):455-64), or Bae K T, Seeck B A, Hildebolt C F, et al: Contrast enhancement in cardiovascular MDCT: effect of body weight, height, body surface area, body mass index, and obesity. (American Journal of Roentgenology 2008; 190(3):777-84). The entire contents of each of these documents is hereby incorporated herein by reference.

The patient information preferably comprises at least a number of parameters. Influencing variables which influence contrast agent distribution can advantageously be taken into account via the method according to at least one embodiment of the invention.

One method variant of at least one embodiment involves deriving an actuation parameter for actuation which comprises at least one parameter from the following list:

start or end of data acquisition, start or end of X-ray exposure via an X-ray source comprised by the imaging device, start or end, acceleration or velocity of movement of a patient positioning apparatus comprised by the imaging device.

The start or end of data acquisition may in particular comprise the acquisition of measurement data on which the generated image data set is based via a detector comprised by the imaging device. Actuation of a patient positioning apparatus comprised by the imaging device with regard to a start, end, acceleration or velocity of a movement based upon the established time information ensures optimum positioning of the patient for data acquisition and/or that measurement data can be suitably acquired for the entire optionally extensive examination region.

Optimum, in particular automatic, actuation of the imaging device for generating the contrast-enhanced image data set can preferably be enabled based upon the first or of the first and the second item(s) of time information. An optimized, patient-specific scan timing for acquiring the measurement data on which the image data set is based is advantageously enabled.

The invention of at least one embodiment furthermore relates to a training method for a trained function for use in a method for actuating an imaging device as claimed in one of the preceding claims comprising the steps of:

first provision of a training item of patient information and a first comparison item of time information linked therewith via a first training interface, application of the trained function to the provided training item of patient information and thus establishment of a first training item of time information via a training computing unit, adaptation of at least one parameter of the trained function based upon a comparison of the training item of time information and the corresponding first comparison item of time information via the training computing unit, second provision of the trained function via a second training interface.

A trained function can advantageously be provided.

The provision of a training item of patient information and of a first comparison item of time information linked therewith may in particular comprise acquiring and/or reading out a computer-readable data storage device and/or receipt from a data storage unit, for example a database. The training item of patient information preferably comprises the same patient-specific parameters which are to be provided in a method for actuating the imaging device. The first comparison item of time information linked therewith preferably comprises that type of time information which is to be established in a method for actuating the imaging device for a patient.

It may furthermore be provided that, in the step of first provision, in addition to a training item of patient information, a second training item of time information is moreover provided via the first training interface and that, in the step of application of the trained function, the trained function is applied to the provided training item of patient information and to the provided second training item of time information, whereby a first training item of time information is established.

The second training item of time information may then for example relate to a point in time of contrast enhancement during an arterial perfusion phase of contrast enhancement at least in the first or in a second subregion, differing from the first, of a training examination region of the training patient. The first training item of time information may then relate to a point in time of contrast enhancement during a perfusion phase subsequent to an arterial perfusion phase of contrast enhancement by the contrast agent in the first subregion, comprising an extravascular part of the training examination region of the training patient.

The second training item of time information may also relate to a point in time of contrast enhancement during an arterial perfusion phase of contrast enhancement at least in a second subregion, differing from the first, of the training examination region of the training patient. The first training item of time information may then relate to a point in time of contrast enhancement during an arterial perfusion phase of contrast enhancement at least in the first subregion.

At least one embodiment of the invention further relates to an apparatus for actuating an imaging device for the acquisition of a contrast agent-enhanced image data set of an examination region of a patient according to a previously described method and the aspects thereof, comprising:

an interface configured to provide an item of patient information of the patient, a computing unit configured to establish a first item of time information relating to a point in time of contrast enhancement by the contrast agent in at least one first subregion of the examination region, based upon the item of patient information by application of a trained function, wherein at least one parameter of the trained function is adapted based upon a comparison between a first training item of time information based on a training item of patient information of a training patient and a first comparison item of time information, wherein the first comparison item of time information is linked with the training item of patient information, and a control unit configured to actuate the imaging device based upon the first item of time information.

The apparatus of at least one embodiment may moreover have a second interface configured to provide a second item of time information.

Such an apparatus for actuating an imaging device may in particular be configured to carry out the previously described method according to the invention for actuating an imaging device and the aspects thereof. The apparatus may be configured to carry out the method and the aspects thereof by the interface or interfaces, the computing unit and the control unit being configured to carry out the corresponding method steps.

The advantages of the proposed apparatus substantially correspond to the advantages of the proposed method for actuating an imaging device. Features, advantages or alternative embodiments mentioned in this connection are likewise also applicable to the apparatus for actuation and vice versa.

At least one embodiment of the invention furthermore relates to an imaging device comprising an apparatus for actuating an imaging device.

The imaging device is here advantageously configured to carry out an embodiment of the proposed method for actuating the imaging device. The advantages of the proposed imaging device substantially correspond to the advantages of the proposed method for actuating the imaging device. Features, advantages or alternative embodiments mentioned in this connection are likewise also applicable to the imaging device and vice versa.

The imaging device may preferably be configured as a CT device.

At least one embodiment of the invention further relates to a training apparatus for providing a trained function for application in a previously described method for actuating a imaging device comprising:

a training interface, configured to provide a training item of patient information and a first comparison item of time information linked therewith, a training computing unit configured to apply the trained function to the provided training item of patient information and thus establish a first training item of time information, wherein the training computing unit is furthermore configured to adapt at least one parameter of the trained function based upon a comparison of the first training item of time information and the corresponding first comparison item of time information, and a second training interface configured to provide the trained function.

Such a training apparatus may in particular be configured to carry out the previously described training method according to the invention for providing a trained function and the aspects thereof. The training apparatus is configured to carry out this method and the aspects thereof by the training interface and the training computing unit being configured to carry out the corresponding method steps. Features, advantages or alternative embodiments mentioned in this connection are likewise also applicable to the training apparatus and vice versa.

At least one embodiment of the invention furthermore relates to a computer program product with a computer program, which can be directly loaded into a storage device of an apparatus for actuating an imaging device, with program parts for carrying out all the steps of one embodiment of the method for actuating an imaging device and the aspects thereof when the program parts are run by the apparatus.

At least one embodiment of the invention furthermore relates to a computer program product with a computer program, which can be directly loaded into a training storage device of a training apparatus, with program parts for carrying out all the steps of at least one embodiment of the training method and the aspects thereof when the program parts are run by the training apparatus.

A computer program product may be a computer program or comprise a computer program. As a consequence, the method according to at least one embodiment of the invention can be carried out in a quick, identically repeatable and robust manner. The computer program product is configured such that it can carry out the method steps according to the invention via the apparatus or training apparatus. The apparatus or training apparatus must here in each case have the prerequisites such as for example an appropriate working memory, an appropriate graphics card or an appropriate logic unit for it to be possible to carry out the respective method steps efficiently. The computer program product is for example stored on a computer-readable medium or stored on a network or server from which it can be loaded into a computing unit or training computing unit of the apparatus or training apparatus.

At least one embodiment of the invention may relate to a computer-readable storage medium on which program parts that can be read and run by the apparatus are stored in order to carry out all the steps of one of at least one embodiment of the methods for actuating an imaging device or the aspects thereof when the program parts are run by the apparatus.

Examples of a computer-readable data storage medium are a DVD, a magnetic tape, a hard disk or a USB stick on which electronically readable control information, in particular software, is stored.

At least one embodiment of the invention may relate to a computer-readable storage medium on which program parts that can be read and run by a training apparatus are stored in order to carry out all the steps of at least one embodiment of the described training method or one of the aspects thereof when the program parts are run by the training apparatus.

A largely software-based implementation has the advantage that processing units and/or training apparatuses which are already in service can also straightforwardly be retrofitted to operate in the manner according to the invention via a software update. In addition to the computer program, a computer program product may comprise additional elements such as for example documentation and/or additional components, as well as hardware components, such as for example hardware keys (dongles etc.) for using the software.

For the purposes of the invention, features which are described in relation to different embodiments of the invention and/or different categories of claim (method, use, apparatus, system, arrangement etc.) may be combined to yield further embodiments of the invention. For example, a claim relating to an apparatus may also be further developed with features which are described or claimed in connection with a method and vice versa. Functional features of a method may in this case be embodied by appropriately configured physical components.

Use of the indefinite article "a" or "an" does not rule out the possibility of the feature in question also being present in multiple instances. Use of the term "have" does not rule out the possibility of the terms linked by the term "have" being identical. For example, the medical imaging apparatus includes the medical imaging apparatus. Use of the term "unit" does not rule out the possibility of the object to which the term "unit" relates including a plurality of components which are spatially separated from one another.

The expression "based upon" may be understood, in the context of the present application, in particular to mean "using". In particular, wording according to which a first feature is generated (or: established, determined etc.) based upon a second feature does not rule out the possibility of the first feature being generated (or: established, determined etc.) based upon a third feature.

FIG. 1 shows a schematic flow chart for an example method variant for actuating an imaging device for the acquisition of a contrast agent-enhanced image data set of an examination region of a patient 39. The method comprises the steps of provision S1, establishment S2 and actuation S3.

In provision step S1, an item of patient information PI is provided via an interface IF1.

The patient information PI preferably comprises at least one parameter from the following list:
a parameter of patient physiology,
a parameter of patient pathology,
a laboratory value for the patient,
patient medication,
a parameter of the contrast agent used or of contrast agent administration,
a (target) organ to be mapped by way of the contrast-enhanced image data set.

In establishment step S2, a first item of time information t1 relating to a point in time of contrast enhancement by a contrast agent in at least one first subregion of the examination region is established via a computing unit CU based upon the item of patient information PI and by application of a trained function TF, wherein at least one parameter of the trained function TF is adapted based upon a comparison between a first training item of time information based on a training item of patient information T-PI of a training patient and a first comparison item of time information, wherein the first comparison item of time information is linked with the training item of patient information. The trained function preferably comprises a neural net.

In actuation step S3, the imaging device 32 is actuated based upon the established first item of time information t1 via a control unit 51, wherein, based upon the first item of time information t1, the contrast agent-enhanced image data set is acquired.

For actuation, an actuation parameter which comprises at least one of the parameters from the following list may be derived in particular at least based upon the first item of time information t1:
start or end of data acquisition via a measurement data acquisition unit comprised by the imaging device, in particular via a detector,
start or end of X-ray exposure via an X-ray source comprised by the imaging device,
start or end, acceleration or velocity of a movement of a patient positioning apparatus of the imaging device.

For example, the first subregion comprises an extravascular part of the examination region and the first item of time information t1 relates to a point in time of contrast enhancement during a perfusion phase subsequent to an arterial perfusion phase of contrast enhancement by the contrast agent, such that structures of relevance to diagnosis in the extravascular region can advantageously be presented in contrast-enhanced manner. The extravascular region may in particular be comprised by a target organ of the patient in the subregion. The patient-specifically established first item of time information t1 advantageously enables an adapted scan timing and actuation coordinated therewith of the imaging device 32, such that an image data set which is particularly advantageous for patient diagnosis can be generated.

FIG. 2 shows a schematic flow chart for a further example method variant of an embodiment for actuating an imaging device 32.

In this variant, provision step S4 provides a second item of time information t2 via a second interface IF2.

For example, the second item of time information t2 then relates to a point in time of contrast enhancement during an arterial perfusion phase of contrast enhancement at least in the first subregion or in a second subregion, differing from the first, of the examination region. The second item of time information t2 may have been determined based upon a test bolus method or based upon a bolus tracking method. The second item of time information t2 may have been determined based upon one of the two methods in combination with a pharmacokinetic model. The second item of time information t2 may have been established for the first subregion. The examination region may for example be an extensive examination region. For example, a second item of time information t2 may have been determined for the second subregion based upon a test bolus method or based upon a bolus tracking method and the first subregion may be remote from the second subregion.

In another example, the first item of time information t1 relates to a point in time of contrast enhancement during an arterial perfusion phase of contrast enhancement at least in the first subregion and the second item of time information t2 relates to a point in time of contrast enhancement during an arterial perfusion phase of contrast enhancement at least in a second subregion, differing from the first, of the examination region. The examination region may for example be an extensive examination region. For example, a second item of time information t2 may have been determined for the second subregion based upon a test bolus method or based upon a bolus tracking method and the first subregion may be remote from the second subregion.

In actuation step S3, the imaging device 32 is then actuated based upon the first item of time information t1 and the second item of time information t2.

The method may moreover comprise a step of presenting S5 the generated image data set.

The method may moreover comprise the step of establishing S6 the second item of time information t2, for example based upon a pharmacokinetic model PKM. A time value determined via a test bolus method or a bolus tracking method may here enter into the establishment of the second item of time information t2.

Figures 3, 4:
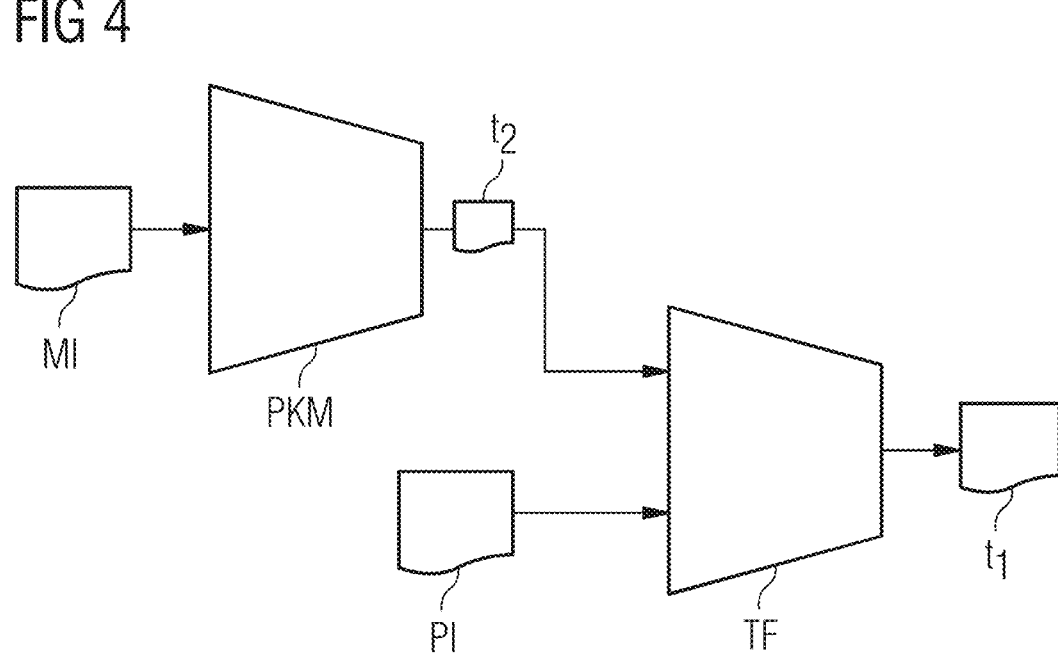
FIG. 3 shows an alternative form of presenting a sequence of an example method variant of an embodiment for actuating an imaging device with reference to data flow.
FIG. 4 shows an alternative form of presenting a sequence of an example method variant of an embodiment for actuating an imaging device with reference to data flow.

FIG. 3 shows an alternative form of presenting a sequence of an example method variant for actuating an imaging device with reference to data flow.

In this variant of an embodiment, the item of patient information PI is provided as an input parameter for the trained function TF. The first item of time information t1 is established based upon the trained function TF.

An item of model information MI is likewise provided for a pharmacokinetic model PKM, by which the second item of time information t2 can be established. The item of model information MI may in particular comprise a value from a bolus tracking method or a test bolus method. The item of model information may moreover in particular comprise an item of information relating to a parameter of the contrast agent used or to contrast agent administration. The item of model information may also comprise an item of information about a subregion, for which the second item of time information t2 is established, and optionally further items of patient information.

The first and the second items of time information are then combined or the second item of time information is adapted by way of the first item of time information, such that an adapted item of time information t3 can be established which can then be used in the actuation step in order actuate the imaging device optimally for generation of the image data set. In this variant, the first item of time information t1 may as a consequence be described as an item of adaptation time information.

In particular, an item of information about the examination region, for example an extent or subregions to be mapped, can also enter as an item of information in the establishment.

FIG. 4 shows an alternative form of presenting a sequence of an example method variant of an embodiment for actuating an imaging device with reference to data flow.

In this variant of an embodiment, the second item of time information t2 enters, in addition to the item of patient information, as an input parameter into the trained function TF to establish a first item of time information t1. In this variant, the first item of time information t1 would already correspond to the adapted item of time information, based upon which actuation can be carried out.

The trained function is in this variant moreover trained via a second training item of time information. In other words, at least one parameter of the trained function TF is adapted based upon a comparison between, on the one hand, a first training item of time information based on a training item of patient information and the second training item of time information of a training patient and, on the other, a first comparison item of time information, wherein the first comparison item of time information is linked with the training item of patient information and the second training item of time information.

Figures 5, 6:
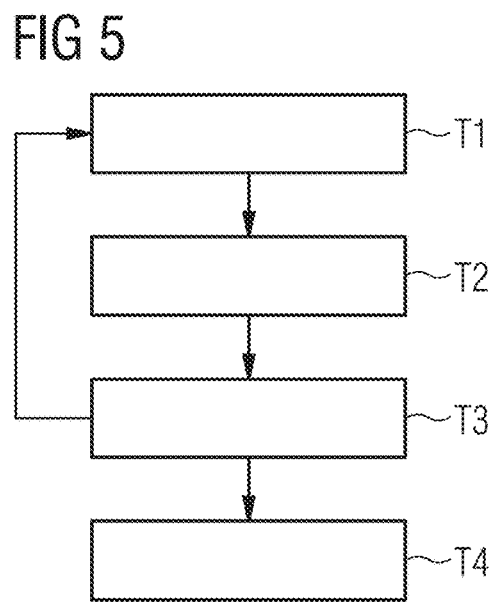
FIG. 5 shows a schematic flow chart for a training method for providing a trained function of an embodiment.
FIG. 6 shows a schematic representation of an apparatus of an embodiment for actuating an imaging device and a schematic representation of a training apparatus for providing a trained function.
Figure 7:
FIG. 7 shows an example imaging device of an embodiment.

FIG. 5 shows a schematic flow chart for a training method of an embodiment for providing a trained function FK.

The training method comprises the steps of first provision T1, application T2, adaptation T3 and second provision T4.

In provision step T1, at least one training item of patient information and a first comparison item of time information linked therewith is provided via a first training interface T-IF1.

In application step T2, the trained function TF is applied to the provided training item of patient information and thus a first training item of time information is established via a training computing unit T-CU.

In adaptation step T3, at least one parameter of the trained function TF is adapted via the training computing unit T-CU based upon a comparison of the first training item of time information and the corresponding first comparison item of time information.

In the second provision step T4, the trained function TF is provided via a second training interface T-IF2.

In particular, a training method can be carried out repeatedly based upon a large number of training items of patient information and comparison items of time information linked therewith.

FIG. 6 shows a schematic representation of an apparatus of an embodiment for actuating an imaging device and a schematic representation of a training apparatus for providing a trained function.

The apparatus SY for actuating an imaging device 32 comprises a first interface IF1 configured to provide S1 an item of patient information PI of the patient 39. The apparatus SY moreover comprises a computing unit CU configured to establish S2 a first item of time information t1 relating to a point in time of contrast enhancement by the contrast agent in at least one first subregion of the examination region, based upon the item of patient information PI by application of a trained function TF, wherein at least one parameter of the trained function TF is adapted based upon a comparison between a first training item of time information based on a training item of patient information T-PI of a training patient and a first comparison item of time information, wherein the first comparison item of time information is linked with the training item of patient information. The apparatus moreover comprises a control unit 51, configured to actuate S3 the imaging device 32 based upon the first item of time information t1.

The apparatus may moreover comprise a storage unit MU.

The apparatus may moreover comprise a second interface IF2. A second item of time information can be provided via the second interface. The control unit 51 may then in particular be configured to actuate the medical device based upon the first item of time information t1 and the second item of time information t2.

The apparatus SY is coupled for signaling in particular with the imaging device 32, such that the imaging device 32 is actuatable via the apparatus SY.

The apparatus SY is in particular configured for carrying out a proposed method of an embodiment for actuating an imaging device 32.

FIG. 6 moreover shows a training apparatus T-SY of an embodiment for providing a trained function.

The training apparatus T-SY comprises a first training interface T-IF1 configured to provide T1 a training item of patient information and a first comparison item of time information linked therewith.

The training apparatus T-SY further comprises a training computing unit T-CU configured to apply T2 the trained function TF to the provided training item of patient information and thus establish a first training item of time information. The training computing unit T-CU is furthermore configured to adapt at least one parameter of the trained function TF based upon a comparison of the first training item of time information and the corresponding first comparison item of time information. The training apparatus T-SY comprises a second training interface T-IF2, configured to provide the trained function TF.

In variant embodiments, the first interface may in particular be configured to provide a second training item of time information. The training computing unit T-CU may in particular be configured to apply the trained function TF to the training item of patient information and the second training item of time information.

The represented training unit T-SY is advantageously configured to carry out a proposed method for providing a trained function.

The apparatus SY and/or the training apparatus T-SY may in particular be a computer, a microcontroller or an integrated circuit. It may alternatively here be a real or virtual group of computers (a technical term for a real group is "cluster", a technical term for a virtual group is "cloud". The apparatus SY and/or the training apparatus T-SY may also be configured as a virtual system which is run on a real computer or a real or virtual group of computers (virtualization).

The interface IF1, IF2 and/or a training interface T-IF1, T-IF2 may be a hardware or software interface (for example PCI bus, USB or FireWire). A computing unit CU and/or a training computing unit T-CU may have hardware elements or software elements, for example a microprocessor or a field programmable gate array (FPGA). A storage unit MU and/or a training storage unit T-MU may be implemented as volatile working memory or random access memory (RAM) or as non-volatile mass storage (hard disk, USB stick, SD card, solid state disk).

The interface IF1, IF2 and/or a training interface T-IF1, T-IF2 may in particular comprise a plurality of subinterfaces. In other words, the interface IF and/or the training interface T-IF may also comprise a large number of interfaces IF or a large number of training interfaces T-IF. The computing unit CU and/or the training computing unit T-CU may in particular comprise a plurality of subcomputing units which carry out the different steps of the respective method. In other words, the computing unit CU and/or the training computing unit T-CU may also be understood as a large number of computing units CU or a large number of training computing units T-CU.

In the example embodiment shown, the apparatus SY is connected via a network NETW to the training apparatus T-SY. For example, a function trained via the training apparatus may be transferred via the network NETW to an apparatus. In the example shown, the apparatus SY is furthermore directly coupled with a medical device 32. In particular, the apparatus may also be comprised by the medical device 32. The apparatus SY may, however, also be connected via the network NETW to the medical imaging device 32.

Communication may furthermore also proceed offline between the apparatus SY and the training apparatus T-SY, for example by an exchange of data storage media.

Communication between the apparatus SY and the training apparatus T-SY may for example consist in the apparatus SY transmitting further training data to the training apparatus T-SY or in the training apparatus T-SY transmitting the trained function to the apparatus SY. The training apparatus T-SY may furthermore be connected to other data sources.

The network NETW may be a local area network ("LAN") or a wide area network ("WAN"). One example of a local network is an intranet while one example of a wide area network is the internet. The network NETW may in particular also take wireless form, in particular as a wireless LAN ("WLAN" or "WiFi") or a Bluetooth connection. The network NETW may also take the form of a combination of the stated examples.

FIG. 8 shows an imaging device 32 in the form of a computed tomography device of an embodiment.

The CT device has a gantry 33 with a rotor 35. The rotor 35 comprises at least one radiation source 37, in particular an X-ray tube, and, positioned opposite, at least one detector 36. The detector 36 and the radiation source 37 are rotatable about a common axis 43 (also denoted axis of rotation). The patient 39 is placed on a patient couch 41 and can be moved along the axis of rotation 43 through the gantry 33. The patient 39 may in general comprise for example an animal patient and/or a human patient.

The CT device 32 comprises a processing unit 45 comprising an apparatus SY for actuating the medical imaging device 32 with a computing unit CU, an interface IF1 and a control unit 51. The processing unit moreover comprises a storage unit MU and a second interface IF2.

An input device 47 and an output device 49 are furthermore connected to the processing unit 45. The input device 47 and the output device 49 may for example enable user interaction, for example manual configuration, confirmation or initiation of a method step. For example, computed tomograph projection data sets and/or a two-dimensional image data set or a three-dimensional image data set may be displayed to the user on the output apparatus 49 comprising a monitor.

Conventionally, measurement data in the form of a large number of (raw) projection data sets of the patient 39 are captured from a plurality of projection angles during relative rotational movement between the radiation source and the patient while the patient 39 is moved continuously or sequentially through the gantry 33 via the patient couch 41.

Then, based upon the projection data sets, a tomographic image data set for a respective z position along the axis of rotation within an examination region can be reconstructed via a mathematical method, for example comprising filtered backprojection or an iterative reconstruction method. Projection data sets from a projection angle range, on which the tomographic image data set is based, are assigned to each tomographic image data set.

A contrast agent bolus can be injected into the patient 39 with the assistance of a contrast agent administration set, such that a contrast-enhanced image data set can be generated.

The apparatus of an embodiment comprised by the processing unit 45 for actuating the imaging device is in particular configured to carry out a method according to the invention for actuating the imaging device 32 for the generation of a contrast agent-enhanced image data set of an examination region of a patient 39.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for actuating an imaging device for acquisition of a contrast agent-enhanced image data set of an examination region of a patient, the method comprising:
    obtaining patient information from a data source, the patient information including a first subregion of the examination region, and the first subregion including an extravascular part of the examination region;
    establishing, via a computing device, first time information by applying a trained function to the patient information, the first time information relating to a first point in time of contrast enhancement by a contrast agent in the first subregion, the first point in time of contrast enhancement corresponding to a first perfusion phase, the first perfusion phase being a hepatic portal venous phase, a nephrogenic phase, a delayed phase or an equilibrium phase in the extravascular part of the examination region, at least one parameter of the trained function being adapted based on a comparison between first training time information and first comparison time information, the first training time information being based on first training patient information, and the first comparison time information being linked with the first training patient information; and
    actuating, via a controller, the imaging device based on the first time information to acquire the contrast agent-enhanced image data set.

2. The method of claim 1, wherein the actuating is based on the first time information and second time information, the second time information relating to a second point in time of contrast enhancement during a first arterial perfusion phase of contrast enhancement in a second subregion of the examination region, and the second subregion differing from the first subregion.

3. The method of claim 2, wherein the establishing of the first time information by application of the trained function is based on the patient information and the second time information, the first training time information being based on the first training patient information and second training time information, and the first comparison time information being linked with the first training patient information and the second training time information.

4. The method of claim 3, wherein
    the first training time information corresponds to the first perfusion phase; and
    the second training time information corresponds to the first arterial perfusion phase.

5. The method of claim 4, wherein
    the first training time information corresponds to the first perfusion phase in the extravascular part of the examination region; and
    the second training time information corresponds to the first arterial perfusion phase in the second subregion of the examination region.

6. The method of claim 2, wherein the second time information has been established based on a pharmacokinetic model in conjunction with one of a test bolus method or a bolus tracking method.

7. The method of claim 2, further comprising:
    adapting the second time information using the first time information to obtain adapted time information,
    wherein the actuating is based on the adapted time information.

8. The method of claim 2, wherein the establishing the first time information establishes the first time information by inputting both the patient information and the second time information into the trained function.

9. The method of claim 1, wherein the patient information comprises at least one of:
    a parameter of patient physiology;
    a parameter of patient pathology;
    a laboratory value for the patient;
    patient medication;
    a parameter of the contrast agent used or of contrast agent administration; or
    an organ to be mapped via the contrast agent-enhanced image data set.

10. The method of claim 1, further comprising:
    deriving an actuation parameter for the actuating, the actuation parameter including at least one parameter of
    a start or end of data acquisition,
    a start or end of X-ray exposure via an X-ray source of the imaging device, or
    a start, end, acceleration or velocity of movement of a patient positioning apparatus, the imaging device including the patient positioning apparatus.

11. The method of claim 1, wherein the trained function includes a neural net.

12. The method of claim 1, wherein the patient information includes at least one among:
    an osmolality of the contrast agent;
    a rheology of the contrast agent;
    an injection site of the contrast agent;
    a volume of the contrast agent;
    an administration duration of the contrast agent; or
    an injection rate of the contrast agent.

13. The method of claim 1, further comprising:
    establishing second time information by applying a pharmacokinetic model to information obtained using one of a test bolus method or a bolus tracking method, the pharmacokinetic model being different from the trained function, wherein the actuating is based on the first time information and the second time information.

14. The method of claim 13, further comprising:

adapting the second time information using the first time information to obtain adapted time information, wherein the actuating is based on the adapted time information.

15. The method of claim 13, wherein the establishing the first time information establishes the first time information by inputting both the patient information and the second time information into the trained function.

16. The method of claim 1, wherein the obtaining includes obtaining the patient information from the data source based on:

input parameters; or parameters corresponding to an examination protocol for generation of the contrast agent-enhanced image data set.

17. The method of claim 1, wherein the first comparison time information corresponds to the first perfusion phase.

18. The method of claim 1, wherein the first subregion includes a liver of the patient, and the first perfusion phase corresponds to the hepatic portal venous phase; or the first subregion includes a kidney of the patient, and the first perfusion phase corresponds to the nephrogenic phase.

19. The method of claim 1, wherein the first subregion includes a kidney of the patient, and the first perfusion phase corresponds to the nephrogenic phase.

20. A training method for provisioning a trained function for application in actuating an imaging device, comprising:

obtaining first training patient information from a data source, the first training patient information being linked to first comparison time information, the first training patient information including a subregion and the sub region including an extravascular part of an examination region;

applying, via a training computing device, the trained function to the first training patient information to establish first training time information, the first comparison time information relating to a point in time of contrast enhancement by a contrast agent in the subregion, the point in time of contrast enhancement corresponding to a hepatic portal venous perfusion phase, a nephrogenic perfusion phase, a delayed perfusion phase or an equilibrium perfusion phase in the extravascular part of the examination region;

adapting, via the training computing device, at least one parameter of the trained function based on a comparison of the first training time information and the first comparison time information; and provisioning, via a training interface, the trained function.

21. An apparatus for actuating an imaging device for acquisition of a contrast agent-enhanced image data set of an examination region of a patient, comprising:

a computing unit configured to obtain patient information from a data source, the patient information including a subregion of the examination region, and the subregion including an extravascular part of the examination region, and establish first time information by applying a trained function to the patient information, the first time information relating to a point in time of contrast enhancement by a contrast agent in the subregion, the point in time of contrast enhancement corresponding to a hepatic portal venous perfusion phase, a nephrogenic perfusion phase, a delayed perfusion phase or an equilibrium perfusion phase in the extravascular part of the examination region, at least one parameter of the trained function being adapted based on a comparison between first training time information and first comparison time information, the first training time information being based on first training patient information, and the first comparison time information being linked with the first training patient information; and a controller configured to actuate the imaging device based on the first time information.

22. A training apparatus for providing a trained function for application in actuating an imaging device, comprising:

a training computing unit configured to obtain first training patient information from a data source, the first training patient information being linked to first comparison time information, and the first training patient information including a subregion, and the subregion including an extravascular part of an examination region, apply the trained function to the first training patient information to establish first training time information, the first comparison time information relating to a point in time of contrast enhancement by a contrast agent in the subregion, the point in time of contrast enhancement corresponding to a hepatic portal venous perfusion phase, a nephrogenic perfusion phase, a delayed perfusion phase or an equilibrium perfusion phase in the extravascular part of the examination region, and adapt at least one parameter of the trained function based on a comparison of the first training time information and the first comparison time information; and a training interface configured to provide the trained function.

* * * * *